(12) United States Patent
Halverson et al.

(10) Patent No.: US 9,314,346 B2
(45) Date of Patent: Apr. 19, 2016

(54) SPINAL IMPLANT

(75) Inventors: Peter Halverson, Alpine, UT (US);
Larry L. Howell, Orem, UT (US);
Spencer P. Magleby, Provo, UT (US);
Anton E. Bowden, Lindon, UT (US)

(73) Assignee: Brigham Young University, Provo, UT (US)

( * ) Notice: Subject to any disclaimer, the term of this patent is extended or adjusted under 35 U.S.C. 154(b) by 500 days.

(21) Appl. No.: 12/726,816

(22) Filed: Mar. 18, 2010

(65) Prior Publication Data
US 2010/0241232 A1    Sep. 23, 2010

Related U.S. Application Data

(63) Continuation-in-part of application No. 12/029,046, filed on Feb. 11, 2008, now Pat. No. 8,308,801.

(60) Provisional application No. 61/210,572, filed on Mar. 19, 2009, provisional application No. 60/901,217, filed on Feb. 12, 2007.

(51) Int. Cl.
*A61F 2/44* (2006.01)
*A61B 17/70* (2006.01)
*A61F 2/30* (2006.01)

(52) U.S. Cl.
CPC .............. *A61F 2/4425* (2013.01); *A61B 17/70* (2013.01); *A61F 2002/30014* (2013.01); *A61F 2002/30016* (2013.01); *A61F 2002/30232* (2013.01);
(Continued)

(58) Field of Classification Search
CPC . A61F 2/4425; A61F 2002/443; A61F 2/442; A61F 2/44
USPC ............................................ 623/17.11–17.16
See application file for complete search history.

(56) References Cited

U.S. PATENT DOCUMENTS 3,945,053 A    3/1976    Hillberry et al.
4,267,608 A    5/1981    Bora, Jr.
(Continued)

FOREIGN PATENT DOCUMENTS

KR    1020050080493    8/2005
KR    1020060113318    11/2006
(Continued)

OTHER PUBLICATIONS

Jeanneau et al.; "A Compliant Rolling Contact Joint and it's Application in a 3-DOF Planar Parallel Mechanism with Kinematic Analysis"; Proceedings of DETC'04, ASME 2004 Design Engineering Technical Conferences and Computers and Information in Engineering Conference; Sep. 28-Oct. 2, 2004; Salt Lake City, Utah USA. DETC2004-57264, 2004by ASME.
(Continued)

*Primary Examiner* — Christian Sevilla
*Assistant Examiner* — Si Ming Ku
(74) *Attorney, Agent, or Firm* — Adam D. Stevens; Kirton McConkie

(57) ABSTRACT

A spinal implant includes a first rolling-contact core operably coupled to a first vertebra, said first rolling-contact core having a first convex surface having a first axis, said first convex surface configured to provide a first rolling motion in a first direction to said first vertebra relative to a second vertebra. At least one flexure is connected to said first rolling-contact core, said flexure configured to constrain said first rolling motion.

31 Claims, 13 Drawing Sheets

(52) U.S. Cl.
CPC .............. *A61F2002/30448* (2013.01); *A61F 2002/30451* (2013.01); *A61F 2002/443* (2013.01); *A61F 2220/005* (2013.01); *A61F 2220/0058* (2013.01); *A61F 2230/0069* (2013.01); *A61F 2250/0018* (2013.01); *A61F 2250/0019* (2013.01); *A61F 2310/00017* (2013.01); *A61F 2310/00023* (2013.01)

(56) References Cited

U.S. PATENT DOCUMENTS

| | | | |
|---|---|---|---|
| 5,405,408 A | 4/1995 | Pitkin | |
| 5,415,661 A | 5/1995 | Holmes | |
| 5,733,285 A | 3/1998 | Errico | |
| 5,772,661 A | 6/1998 | Michelson | |
| 5,964,760 A | 10/1999 | Richelsoph | |
| 6,045,552 A | 4/2000 | Zucherman et al. | |
| 6,355,040 B1 | 3/2002 | Richelsoph | |
| 6,379,354 B1 | 4/2002 | Rogozinski | |
| 6,440,169 B1 | 8/2002 | Elberg | |
| 6,527,804 B1 | 3/2003 | Gauchet et al. | |
| 6,540,785 B1 | 4/2003 | Gill et al. | |
| 6,572,653 B1 | 6/2003 | Simonson | |
| 6,579,320 B1 | 6/2003 | Gauchet et al. | |
| 6,610,093 B1 * | 8/2003 | Pisharodi | 623/17.15 |
| 6,645,248 B2 | 11/2003 | Casutt | |
| 6,723,127 B2 | 4/2004 | Ralph et al. | |
| 6,793,678 B2 | 9/2004 | Hawkins | |
| 6,802,867 B2 | 10/2004 | Manasas et al. | |
| 6,811,567 B2 | 11/2004 | Reiley | |
| 6,863,688 B2 | 3/2005 | Ralph et al. | |
| 6,936,071 B1 | 8/2005 | Marnay et al. | |
| 6,949,123 B2 | 9/2005 | Reiley | |
| 6,964,666 B2 | 11/2005 | Jackson | |
| 6,966,910 B2 | 11/2005 | Ritland | |
| 6,974,478 B2 | 12/2005 | Reiley et al. | |
| 6,983,924 B2 | 1/2006 | Howell et al. | |
| 6,991,632 B2 | 1/2006 | Ritland | |
| 6,997,955 B2 | 2/2006 | Zubok et al. | |
| 7,029,475 B2 | 4/2006 | Panjabi | |
| 7,074,238 B2 | 7/2006 | Stinson et al. | |
| 7,093,827 B2 | 8/2006 | Culpepper | |
| 7,115,129 B2 | 10/2006 | Heggeness | |
| 7,144,396 B2 | 12/2006 | Shluzas | |
| 7,207,992 B2 | 4/2007 | Ritland | |
| 7,229,441 B2 | 6/2007 | Trieu et al. | |
| 7,270,682 B2 * | 9/2007 | Frigg et al. | 623/17.16 |
| 7,326,210 B2 | 2/2008 | Jahng et al. | |
| 7,338,398 B2 | 3/2008 | Whiting et al. | |
| 7,361,196 B2 | 4/2008 | Fallin et al. | |
| 7,371,238 B2 | 5/2008 | Soboleski et al. | |
| 7,377,942 B2 | 5/2008 | Berry | |
| 7,445,635 B2 | 11/2008 | Fallin et al. | |
| 7,458,981 B2 | 12/2008 | Fielding et al. | |
| 7,476,238 B2 | 1/2009 | Panjabi | |
| 7,476,251 B2 | 1/2009 | Zucherman et al. | |
| 7,481,830 B2 | 1/2009 | Wall et al. | |
| 7,485,133 B2 | 2/2009 | Cannon et al. | |
| 7,485,134 B2 | 2/2009 | Simonson | |
| 7,485,146 B1 * | 2/2009 | Crook et al. | 623/17.15 |
| 7,491,218 B2 | 2/2009 | Landry et al. | |
| 7,491,238 B2 | 2/2009 | Arnin et al. | |
| 7,491,240 B1 | 2/2009 | Carver et al. | |
| 7,494,507 B2 | 2/2009 | Dixon et al. | |
| 7,537,615 B2 | 5/2009 | Lemaire | |
| 7,618,441 B2 | 11/2009 | Groiso | |
| 7,632,292 B2 | 12/2009 | Sengupta et al. | |
| 7,682,375 B2 | 3/2010 | Ritland | |
| 7,785,351 B2 | 8/2010 | Gordon et al. | |
| 7,909,877 B2 * | 3/2011 | Krueger et al. | 623/17.15 |
| 8,025,681 B2 | 9/2011 | Colleran et al. | |
| 2002/0138077 A1 | 9/2002 | Ferree | |
| 2003/0171751 A1 | 9/2003 | Ritland | |
| 2004/0002708 A1 | 1/2004 | Ritland | |
| 2004/0176849 A1 | 9/2004 | Zubok et al. | |
| 2005/0101954 A1 | 5/2005 | Simonson | |
| 2005/0113924 A1 | 5/2005 | Buttermann | |
| 2005/0113927 A1 | 5/2005 | Malek | |
| 2005/0125065 A1 | 6/2005 | Zucherman et al. | |
| 2005/0149023 A1 | 7/2005 | Ritland | |
| 2005/0159818 A1 * | 7/2005 | Blain | 623/17.15 |
| 2005/0165487 A1 | 7/2005 | Muhanna | |
| 2005/0177156 A1 | 8/2005 | Timm et al. | |
| 2005/0240270 A1 | 10/2005 | Zubok et al. | |
| 2005/0261772 A1 | 11/2005 | Filippi et al. | |
| 2006/0009768 A1 | 1/2006 | Ritland | |
| 2006/0009850 A1 | 1/2006 | Frigg et al. | |
| 2006/0036240 A1 | 2/2006 | Colleran | |
| 2006/0041314 A1 | 2/2006 | Millard | |
| 2006/0052784 A1 | 3/2006 | Dant et al. | |
| 2006/0084987 A1 | 4/2006 | Kim | |
| 2006/0190079 A1 | 8/2006 | Istephanous et al. | |
| 2006/0229609 A1 | 10/2006 | Wang | |
| 2006/0240533 A1 | 10/2006 | Sengupta et al. | |
| 2006/0271047 A1 | 11/2006 | Jackson | |
| 2006/0271051 A1 | 11/2006 | Berrevoets | |
| 2007/0016193 A1 | 1/2007 | Ritland | |
| 2007/0028714 A1 | 2/2007 | Lusk et al. | |
| 2007/0043365 A1 | 2/2007 | Ritland | |
| 2007/0049936 A1 | 3/2007 | Colleran et al. | |
| 2007/0088440 A1 * | 4/2007 | Eisermann et al. | 623/17.14 |
| 2007/0179618 A1 | 8/2007 | Trieu et al. | |
| 2008/0015588 A1 | 1/2008 | Hawkes | |
| 2008/0077246 A1 | 3/2008 | Fehling et al. | |
| 2008/0140075 A1 | 6/2008 | Ensign | |
| 2008/0183209 A1 | 7/2008 | Robinson et al. | |
| 2008/0195208 A1 | 8/2008 | Castellvi | |
| 2008/0195213 A1 * | 8/2008 | Halverson et al. | 623/17.16 |
| 2008/0312693 A1 | 12/2008 | Trautwein | |
| 2009/0005819 A1 | 1/2009 | Ben-Mokhtar et al. | |
| 2009/0048631 A1 | 2/2009 | Bhatnagar et al. | |
| 2009/0228045 A1 | 9/2009 | Hayes et al. | |
| 2009/0259257 A1 | 10/2009 | Prevost | |
| 2009/0270921 A1 | 10/2009 | Krause | |
| 2010/0204732 A1 | 8/2010 | Aschmann | |
| 2010/0211106 A1 | 8/2010 | Bowden | |
| 2010/0217324 A1 | 8/2010 | Bowden et al. | |
| 2010/0217326 A1 | 8/2010 | Bowden et al. | |
| 2010/0217334 A1 | 8/2010 | Hawkes | |
| 2010/0222821 A1 | 9/2010 | Bowden et al. | |
| 2010/0222823 A1 | 9/2010 | Bowden et al. | |

FOREIGN PATENT DOCUMENTS

| | | |
|---|---|---|
| WO | WO 2004/071344 | 8/2004 |
| WO | WO 2005/051243 | 6/2005 |
| WO | WO 2005/107654 | 11/2005 |
| WO | WO 2006127992 | 11/2006 |
| WO | WO 2008/070840 | 6/2008 |
| WO | WO 2008/100891 | 8/2008 |
| WO | WO 2010/096621 | 8/2010 |
| WO | WO 2010/096829 | 8/2010 |
| WO | WO 2010/108010 | 9/2010 |

OTHER PUBLICATIONS

Cannon et al.; "Compliant Rolling-Contact Element Mechanisms"; Proceedings of IDETC/CIE 2005, 2005 ASME Design Engineering Technical Conferences & Computers and Information in Engineering Conference, Sep. 24-28, 2005, 2005; Long Beach, California, USA; DETC2005-84073.

Halverson et al.; "Concepts for Achieving Multi-Stability in Compliant Rolling-Contact Elements"; Proceedings of IDETC/CIE 2007; ASME 2007 International Design Engineering Technical Conferences & Computers and Information in Engineering Conference; Sep. 24-28, 2007; Las Vegas, USA; DETC2007-34836.

Halverson et al.; Tension-Based Multi-Stable Compliant Rolling-Contact Elements: 13th National Conference on Mechanisms and Machines (NaCoMM-2007); IISc, Bangalore, India; Dec. 12-13, 2007.

Jacobsen et al.; "Components for the Design of Lamina Emergent Mechanism"; Proceedings of IMECE 2007, 2007 ASME Interna-

(56) References Cited

OTHER PUBLICATIONS tional Mechanical Engineering Congress and Exposition; Nov. 10-16, 2007; Seattle, USA.
Jacobsen et al.; "Mechanism and Machine Theory"; Mechanism and Machine Theory; 2009; pp. 2098-2109; vol. 44; Elsevier.
Stratton et al.; Force-Displacement Model of the Flexsure™ Spinal Implant; Proceedings of the ASME 2010 International Design Engineering Technical Conferences and Computers and Information in Engineering Conference IDETC/CIE 2010; Aug. 15-18; Montreal, Quebec, Canada.
U.S. Appl. No. 12/916,110, filed Oct. 29, 2010; Spencer P. Magleby.
U.S. Appl. No. 11/952,709, filed Dec. 7, 2007; Michael D. Ensign; office action received Sep. 24, 2010.
PCT Application PCT/US2010/025101; filing date Feb. 23, 2010; David Hawkes; ISR mailed Sep. 27, 2010.
PCT Application PCT/US2007/086803; filing date Dec. 7, 2007; Michael D. Ensign; ISR mailed May 19, 2008.
PCT Application PCT/US2008/053661; filing date Feb. 12, 2008; Peter Halverson; ISR mailed Jun. 5, 2008.
PCT Application PCT/US2010/024674; filing date Feb. 19, 2010; Anton E. Bowden; ISR mailed Nov. 19, 2010.
PCT Application PCT/US2010/027826; filing date Mar. 18, 2010; Peter A. Halverson; ISR mailed Jan. 17, 2011.
U.S. Appl. No. 12/709,240, filed Feb. 19, 2010; Anton E. Bowden; office action issued Dec. 30, 2011.
U.S. Appl. No. 11/952,709, filed Dec. 7, 2007; Michael D. Ensign; office action mailed Mar. 17, 2011.
U.S. Appl. No. 12/916,110, filed Oct. 29, 2010; Spencer P. Magleby; office action issued Mar. 16, 2012.
U.S. Appl. No. 12/711,131, filed Feb. 23, 2010; David T. Hawkes; office action issued Jun. 4, 2012.
U.S. Appl. No. 120/029,046, filed Feb. 11, 2008; Peter Halverson; office action issued Apr. 20, 2012.
U.S. Appl. No. 12/709,240, filed Feb. 19, 2010; Anton E. Bowden; office action dated Jul. 11, 2012.
U.S. Appl. No. 12/709,240, filed Feb. 19, 2010; Anton E. Bowden; office action issued Aug. 29, 2011.
U.S. Appl. No. 12/709,243, filed Feb. 19, 2010; Anton E. Bowden; office action issued Sep. 1, 2011.
U.S. Appl. No. 12/709,248, filed Feb. 19, 2010; Anton E. Bowden; office action issued Sep. 13, 2011.
U.S. Appl. No. 12/709,255, filed Feb. 19, 2010; Anton E. Bowden; office action issued Sep. 15, 2011.
U.S. Appl. No. 12/029,046, filed Feb. 11, 2008; Peter Halverson; office action issued Sep. 22, 2011.
U.S. Appl. No. 12/709,246, filed Feb. 19, 2010; Anton E. Bowden; office action issued Sep. 1, 2011.
U.S. Appl. No. 12/916,110, filed Oct. 29, 2012; Spencer P. Magleby; office action dated Dec. 14, 2012.
U.S. Appl. No. 12/711,131, filed Feb. 23, 2010; David T. Hawkes; office action dated Dec. 26, 2012.
PCT/US2012/041360; filed Jun. 7, 2012; Brigham Young University, et al.; search report dated Dec. 14, 2014.
U.S. Appl. No. 12/709,240, filed Feb. 19, 2010; Anton E. Bowden; office action dated Apr. 22, 2013.
U.S. Appl. No. 12/709,240, filed Feb. 19, 2010; Anton E. Bowden; Notice of Allowance issued Oct. 15, 2013.

\* cited by examiner

Anterior ←——→ Posterior

SPINAL IMPLANT

PRIORITY CLAIM

This application is a continuation-in-part of U.S. patent application Ser. No. 12/029,046, now U.S. Pat. No. 8,308, 801, which claimed the benefit of and priority from U.S. Provisional Patent Application No. 60/901,217 filed on Feb. 12, 2007, and claims the benefit of and priority from U.S. Provisional Patent Application No. 61/210,572 filed on Mar. 19, 2009, which is incorporated herein in its entirety for all purposes by this reference.

FIELD

Embodiments of the present invention relate generally to spinal implants and, more particularly, to intervertebral disc prostheses.

BACKGROUND

The human spine functions through a complex interaction of several parts of the anatomy. FIGS. 1 and 2 (FIG. 2 being the cross-section A-A of FIG. 1) illustrate a segment of the spine 4, with vertebra 5. The vertebra 5 includes the vertebral body 6, the spinous process 8, transverse process 10, pedicle 12, and laminae 14. A functional spine, comprising several vertebra 5, typically subcategorized as being part of the cervical, thoracic, lumbar, sacral, and coccygeal regions as known, provides support to the head, neck, trunk, transfers weight to lower limbs, protects the spinal cord 20, from which peripheral nerves 32 extend, and maintains the body in an upright position while sitting or standing.

Also illustrated in FIGS. 1 and 2, the spinal segment 4 includes intervertebral discs 20 that separate adjacent vertebra 5. The intervertebral discs 20 provide motion, load bearing and cushioning between adjacent vertebrae 5. Intervertebral discs 20 are the largest avascular structure in the body, relying on diffusion for nutrition. The diffusion of nutrients is aided by the compression cycles that the intervertebral discs 20 undergo during the course of normal movement, which drives out waste products and cycles fluids. Lying down and resting reduces the load on the intervertebral discs 20 allowing nutrients to diffuse into the intervertebral discs 20.

Also illustrated in FIGS. 1 and 2, the spinal segment 4 includes spinal facet joints 16. Spinal facet joints 16 join the adjacent vertebrae 6. The spinal facet joints 16 are synovial joints that function much like those of the fingers. Together with the intervertebral disc 20, the spinal facet joints 16 function to provide proper motion and stability to a spinal segment 4. Thus, each spinal segment 4 includes three joints: the intervertebral disc 20 in the anterior aspect of the spinal segment 4 and the two spinal facet joints 16 in the posterior aspect of the spinal segment 4.

For the spinal segment 4 to be healthy, each of the intervertebral disc 20 and the spinal facet joints 16 must be healthy. To remain healthy these joints require motion. The intervertebral disc 20 and the spinal facet joints 16 function together to provide both quality and quantity of motion. The quality of the motion is a exhibited by the non-linear energy storage (force-deflection, torque-rotation) behavior of the spinal segment 4. The quantity of motion is the range of segmental rotation and translation.

Back pain due to diseased, damaged, and/or degraded intervertebral discs 20 and/or spinal facet joints 16 is a significant health problem in the United States and globally. A non-exhaustive and non-limiting illustration of examples of diseased and/or damaged intervertebral discs is shown in FIG. 3. While a healthy intervertebral disc 20 is illustrated at the top of the spine segment 18, diseased and/or damaged discs are also illustrated. The diseased and/or damaged discs include a degenerated disc 22, a bulging disc 24, a herniated disc 25, a thinning disc 26, discs indicating symptoms of degeneration with osteophyte formation 28, as well as hypertrophic spinal facets 29.

A degenerating spinal segment 18 is believed to be the product of adverse changes to its biochemistry and biomechanics. These adverse changes create a degenerative cascade affecting the quality and/or quantity of motion and may ultimately lead to pain. For example, as the health of a spinal segment 18 degenerates and/or changes, the space through which the spinal cord 30 and peripheral nerves 32 (FIGS. 1 and 2) pass can become constricted and thereby impinge a nerve, causing pain. For example, the spinal cord 30 or peripheral nerves 32 may be contacted by a bulging disc 24 or herniated disc 25 or hypertrophic spinal facet 29 as illustrated in FIG. 3. As another example, a change in the spinal segment 18, such as by a thinning disc 26 may alter the way in which the disc functions, such that the disc and spinal facets may not provide the stability or motion required to reduce muscle, ligament, and tendon strain. In other words, the muscular system is required to compensate for the structural deficiency and/or instability of the diseased spinal segment 18, resulting in muscle fatigue, tissue strain, and hypertrophy of the spinal facets, further causing back pain. The pain this causes often leads patients to limit the pain-causing motion. However, this limiting of motion, while offering temporary relief, may result in longer-term harm because the lack of motion limits the ability of the disc to expel waste and obtain nutrients as discussed above.

In many instances of degenerative disc disease, fusion of the vertebrae is the standard of care for surgical treatment, illustrated in FIG. 4. In the U.S. alone, approximately 349,000 spinal fusions are performed each year at an estimated cost of $20.2 billion. The number of lower back, or lumbar, fusions performed in the U.S. is expected to grow to approximately 5 million annually by the year 2030 as the population ages, an increase of 2,200%.

Spinal fusion aims to limit the movement of the vertebra that are unstable or causing a patient pain and/or other symptoms. Spinal fusion typically involves the removal of a diseased disc 50, illustrated in outline in FIG. 4. The removed disc 50 is replaced by one or more fusion cages 52, which are filled or surrounded by autograft bone that typically is harvested by excising one or more spinal facet joints 57. Vertebral bodies 51 adjacent the removed disc 50 are stabilized with one or more posterior supports 58 that are fixedly connected to the vertebral bodies 51 with the use of pedicle screws 54 that are screwed—such as by use of a bolt-style head 56 to turn the pedicle screw 54—into a hole drilled into the pedicle 12 of the vertebral bodies 51.

Fusion, however, often fails to provide adequate or sufficient long-term relief in about one-half of the treatments, resulting in low patient satisfaction. Further, fusion, by definition, restricts the overall motion of the treated functional spine unit, imposing increased stresses and limiting range of motion on those portions of the spinal segment adjacent to the fused vertebral bodies 51. Fusion of a spinal segment has been indicated as a potential cause of degeneration to segments adjacent to the fusion. The adjacent spinal facet joints 57 and adjacent discs 59 often have to bear a greater load as a result of the fusion than would typically be the case, leading to possible overloading and, in turn, degeneration. Thus, surgical fusion often provides short-term relief, but possibly greater long-term spinal degradation than would otherwise have occurred.

Thus, a challenge to alleviating the back pain associated with various ailments is to find an intervertebral disc prosthesis that provides sufficient freedom of movement to at least reduce the risk to the functional health of the adjacent spinal segments, and/or facet joints, and/or discs that are otherwise compromised or have their functional health degraded by spinal fusion, and, more preferably, maintain the functional health of the adjacent spinal segments and/or facet joints and/or discs. Further, an intervertebral prosthesis optionally provides sufficient stability to the diseased segment to alleviate pain and/or other symptoms.

A further challenge is simply the complex, multi-dimensional nature of movement associated with a functional spine unit. Illustrated in FIG. 5 are the varying axes around which a functional spine unit moves. For example, a vertebra 5 is illustrated with an X-axis 60, around which a forward bending motion, or flexion, 61 in the anterior direction occurs. Flexion 61 is the motion that occurs when a person bends forward, for example. A rearward bending motion, or extension, 62 is also illustrated. The Y-axis 63 is the axis around which lateral extension, or bending, 64, left and right, occurs. The Z-axis 65 is the axis around which axial rotation 66, left and right, occurs. Spinal fusion, as discussed above, limits or prevents flexion 61-extension 62, but also limits or prevents motion in lateral extension, or bending, 64 and axial rotation 66. Thus, an improved alternative remedy to fusion preferably allows for movement with improved stability around each of the three axes, 60, 63, and 65.

Another difficulty associated with the complex motion of the spine is that the center-of-rotation for movement around each of the X-axis 60, Y-axis 63, and Z-axis 65 differs for each axis. This is illustrated in FIG. 6, in which the center-of-rotation for the flexion 61-extension 62 motion around the X-axis 60 is located at flexion-extension center-of-rotation 70. The center-of-rotation for the lateral extension, or bending, 64 motion around the Y-axis 63 is located at lateral extension, or bending, center-of-rotation 73. The center-of-rotation for the axial rotation 66 around the Z-axis 65 is located at axial rotation center-of-rotation 75. For more complex motion patterns (e.g., combined flexion, lateral extension/bending, etc.) a two-dimensional representation of the center-of-rotation is inadequate, but the three-dimensional equivalent called the helical axis of motion, or instantaneous screw axis can be employed. Intervertebral disc prostheses that force rotation of a spinal segment around any axis other than the natural helical axis impose additional stresses on the tissue structures at both the diseased spinal segments and the adjacent spinal segments. Compounding the issue for the centers-of-rotation is that they actually change location during the movement, i.e., the location of the centers-of-rotation are instantaneous, which is sometimes referred to as the helical axis. Thus, a preferable remedy to spinal problems would account for the helical axis throughout the range of motion. Stated differently, a preferable intervertebral disc prosthesis would allow the diseased spinal segment and adjacent spinal segments to undergo motion approximate that of the natural helical axis through the range of motions.

Many previous efforts have been made to solve at least some of the problems associated with spinal fusion, but with varying degrees of success. For example, U.S. Patent Publication No. 2008/0195213 filed on Feb. 11, 2008 to several of the present inventors, discloses an intervertebral disc prosthesis that provides for motion in two directions, typically flexion-extension and lateral extension/bending, but not for axial rotation. (U.S. Patent Publication No. 2008/0195213 is incorporated herein in its entirety for all purposes by this reference.)

Thus, there exists a need for an intervertebral disc prosthesis that provides for flexion-extension, lateral extension/bending, and axial rotation.

Further, there exists a need for an intervertebral spinal prosthesis that reduces the stress on a diseased and/or damaged spinal segment without overloading the adjacent discs and vertebrae that could initiate progressive degeneration or diseases in the adjacent discs and vertebrae.

A need also exists for a spinal implant that provides for proper force-deflection behavior of the spinal implant (kinetics)—as noted above in the discussion of FIG. 5—preferably to approximate those of a normal, functional spine unit to relieve the load and strain on the adjacent intervertebral discs, to protect the spinal facet joints, to reduce the risk of damage to segments of the spine adjacent to the diseased segment, to reduce muscle fatigue and reduce and/or eliminate subsequent pain.

A need also exists for a spinal implant that exhibits kinematics—such as the limits of the ranges-of-motion and the centers-of-rotation noted above in the discussion of FIG. 6—that, preferably, are maintained near those of a functional spine unit to maintain an effective range of motion for the intervertebral discs, spinal facet joints, muscles, ligaments, and the tendons around the spine and to reduce the amount of neural element strain, e.g., the strain on the spinal cord and/or other parts of the nervous system.

SUMMARY

Various features and embodiments of the invention disclosed herein provide robust and durable intervertebral disc prostheses that accommodate motion in three axes as compared to a single axis and/or double axes of motion of the prior art.

Embodiments of the invention include a spinal implant, such as an intervertebral disc prosthesis to replace an intervertebral disc that is removed from between two vertebra. Thus, embodiments of the spinal implant optionally are positioned between a first and a second vertebra. The spinal implant includes a first rolling-contact core that is operably coupled to the first vertebra. The rolling-contact core includes a convex surface having a first axis, the convex surface providing a rolling motion in a first direction to the vertebra coupled to the rolling-contact core relative to a second vertebra. At least one flexure optionally connected to the first rolling-contact core constrains, at least in part, the rolling motion of the first rolling-contact core.

Optionally, embodiments of the invention include a second rolling-contact core that is operably coupled to the first rolling-contact core. The second rolling-contact core also includes a second convex surface having a second axis rotated from the first axis, the second convex surface providing a rolling motion in a second direction to the first vertebra relative to the second vertebra. At least another flexure optionally connected to the second rolling-contact core constrains, at least in part, the rolling motion of the second rolling-contact core.

In various embodiments, at least one of the flexures and the rolling-contact cores are coupled or secured directly to the vertebra. Alternatively, embodiments of the invention include end plates, to which the flexures and rolling-contact cores are coupled. The end plates are secured to the first and second vertebra, thereby coupling the rolling-contact cores to the vertebrae.

Optionally, embodiments of the spinal implant include an axial-rotation core operably coupled to at least the first rolling-contact core. The axial-rotation core is configured to provide rotation to the first vertebra relative to the second vertebra around an axis orthogonal to the first axis and/or the second axis. The axial-rotation core optionally includes another flexure connected thereto that constrains, at least in part, the rotation.

Embodiments of the spinal implant include a geometry that, once implanted, is configured to allow flexion-extension, and/or lateral extension/bending, and/or axial rotation with an instantaneous or near-instantaneous centers-of-rotation for the diseased and/or damaged spinal segment and/or adjacent vertebrae and/or spinal facet joints and/or discs that are similar to that of a healthy spinal segment. Thus, the spinal implant restores, to a degree, close to normal movement of the diseased and/or damaged spinal segment and adjacent vertebrae and/or spinal facet joints and/or discs, which, in turn, aids in maintaining the health of adjacent vertebra and/or spinal facet joints and/or discs.

Other embodiments of the spinal implant provide protection to the spine, discs, spinal cord, and peripheral nerves by reducing the risk of harmful, damaging, and/or painful movements while still providing a sufficient range of motion to reduce the risk to adjacent vertebrae and/or spinal facet joints and/or intervertebral discs becoming diseased and/or damaged from lack of sufficient movement. Embodiments of the spinal implant do so by reducing the stresses on a diseased and/or damaged spinal segment from which an intervertebral disc is removed without overloading the adjacent spinal segments, including the adjacent intervertebral discs, spinal facet joints, and vertebrae, that could initiate progressive degeneration or diseases in the adjacent spinal segments.

Additionally, embodiments of the spinal implant preferably provide proper motion—such as the centers-of-rotation, whether instantaneous or otherwise, limits of the ranges-of-motion, and the types of motion—that are maintained near those of a functional spine unit to maintain an effective range of motion for the muscles and the tendons around the spine and to reduce the amount of spinal cord strain.

Embodiments of the spinal implant are preferably made of biocompatible materials, including, but not limited to, biocompatible polymers and plastics, stainless steel, titanium, nitinol, shape-memory materials and/or alloys, and other similar materials.

Embodiments of methods of using the spinal implant are also disclosed.

As used herein, "at least one," "one or more," and "and/or" are open-ended expressions that are both conjunctive and disjunctive in operation. For example, each of the expressions "at least one of A, B and C," "at least one of A, B, or C," "one or more of A, B, and C," "one or more of A, B, or C" and "A, B, and/or C" means A alone, B alone, C alone, A and B together, A and C together, B and C together, or A, B and C together.

Various embodiments of the present inventions are set forth in the attached figures and in the Detailed Description as provided herein and as embodied by the claims. It should be understood, however, that this Summary does not contain all of the aspects and embodiments of the one or more present inventions, is not meant to be limiting or restrictive in any manner, and that the invention(s) as disclosed herein is/are and will be understood by those of ordinary skill in the art to encompass obvious improvements and modifications thereto.

Additional advantages of the present invention will become readily apparent from the following discussion, particularly when taken together with the accompanying drawings.

BRIEF DESCRIPTION OF THE DRAWINGS

To further clarify the above and other advantages and features of the one or more present inventions, reference to specific embodiments thereof are illustrated in the appended drawings. The drawings depict only exemplary embodiments and are therefore not to be considered limiting. One or more embodiments will be described and explained with additional specificity and detail through the use of the accompanying drawings in which.

The drawings are not necessarily to scale.

DETAILED DESCRIPTION

As noted above, the kinetics and kinematics of the spine are quite complex, involving three separate axes around which motion occurs and three separate centers-of-rotation for the different motions. Applicants have recognized that previous spinal implants often address just one form of motion, typically flexion and extension, often through the use of springs of some type that flex and compress. Efforts to address more than one mode of rotation or motion typically tend to be complex, large, and often do not address each individual motion as effectively as devices dedicated to a single motion.

Figure 7:
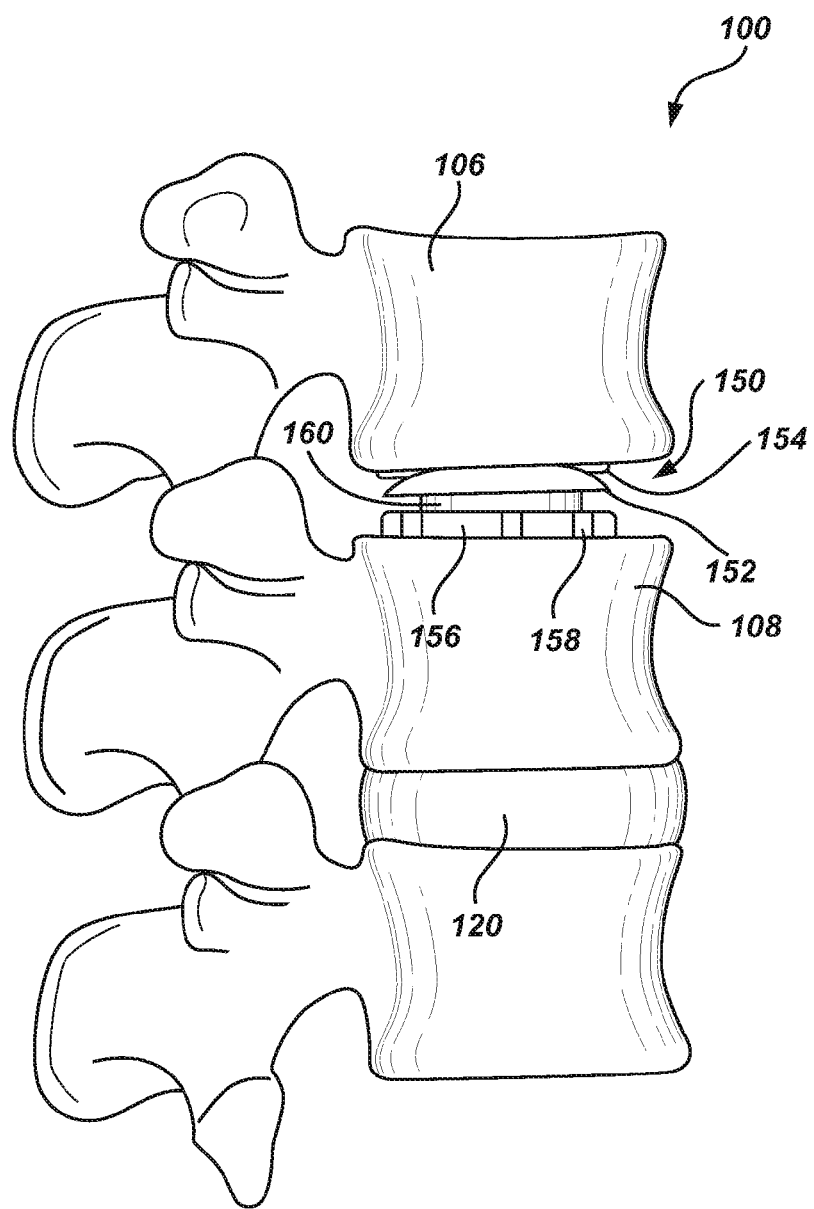
FIG. 7 illustrates an embodiment of a spinal implant, shown from the lateral/side view implanted and coupled directly to a first vertebra and a second vertebra.
Figure 8:
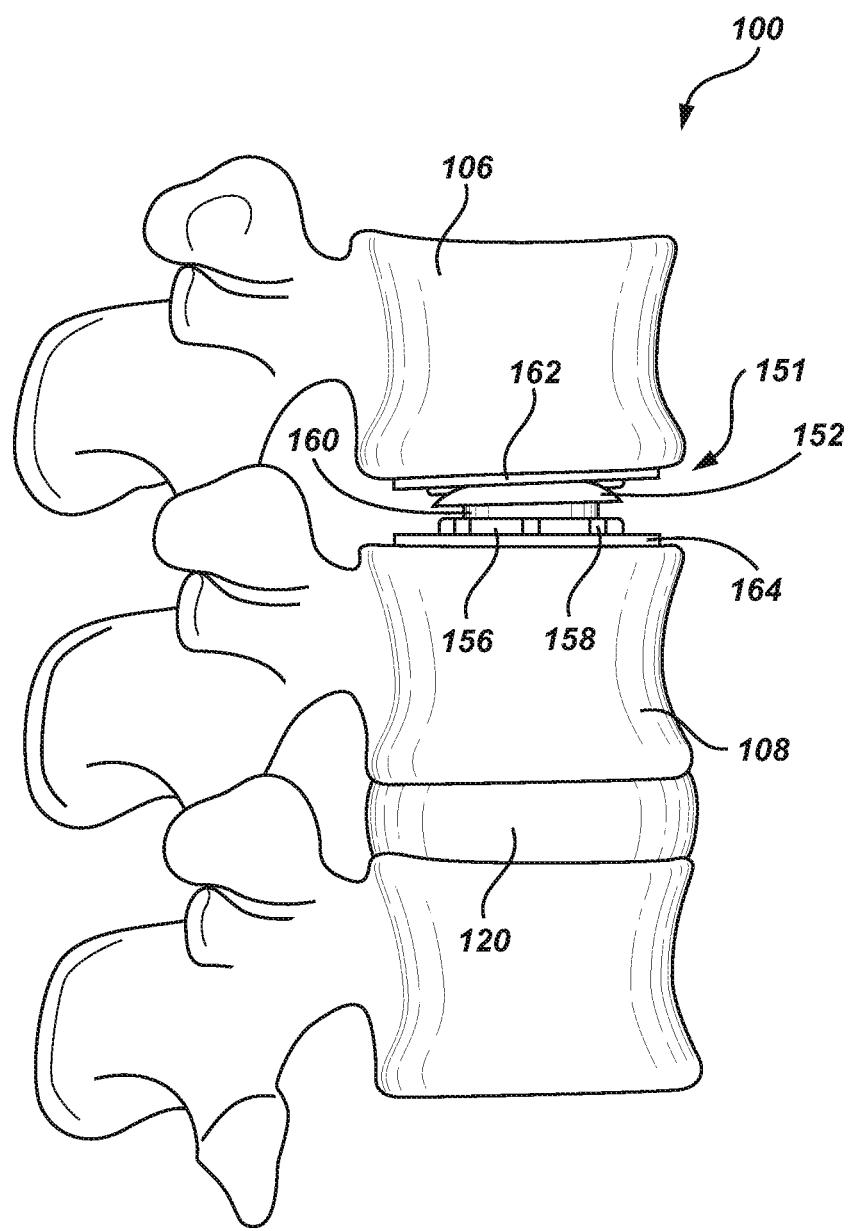
FIG. 8 illustrates an embodiment of a spinal implant, shown from the lateral/side view implanted and coupled to optional end plates, the end plates secured to a first vertebra and a second vertebra.

Turning to FIGS. 7 and 8, embodiments of a spinal implant 150 and 151, such as an intervertebral disc prosthesis, are illustrated positioned between a first vertebra 106 and a second vertebra 108 of a spinal segment 100 in a space where an intervertebral disc (e.g., intervertebral disc 120) has been removed.

Referring to FIGS. 7 and 8, each of the embodiments of the spinal implant 150, 151 include a first rolling-contact core 152. The first rolling-contact core 152 optionally includes at least one flexure 154. The spinal implant 150, 151 optionally includes a second rolling-contact core 156 that optionally includes at least another flexure 158. The spinal implant 151 in FIG. 8 optionally includes a first end plate 162 and a second end plate 164.

Figure 9:
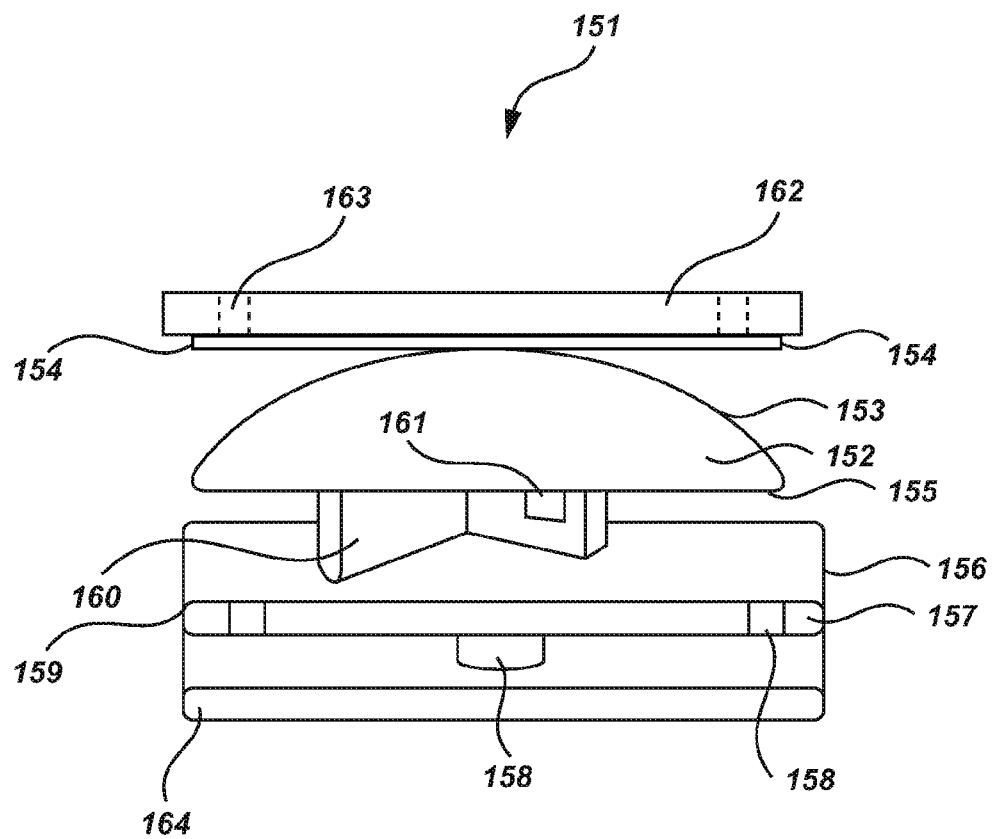
FIG. 9 illustrates lateral/side view of an embodiment of the spinal implant that optionally includes an axial-rotation core.
Figure 10:
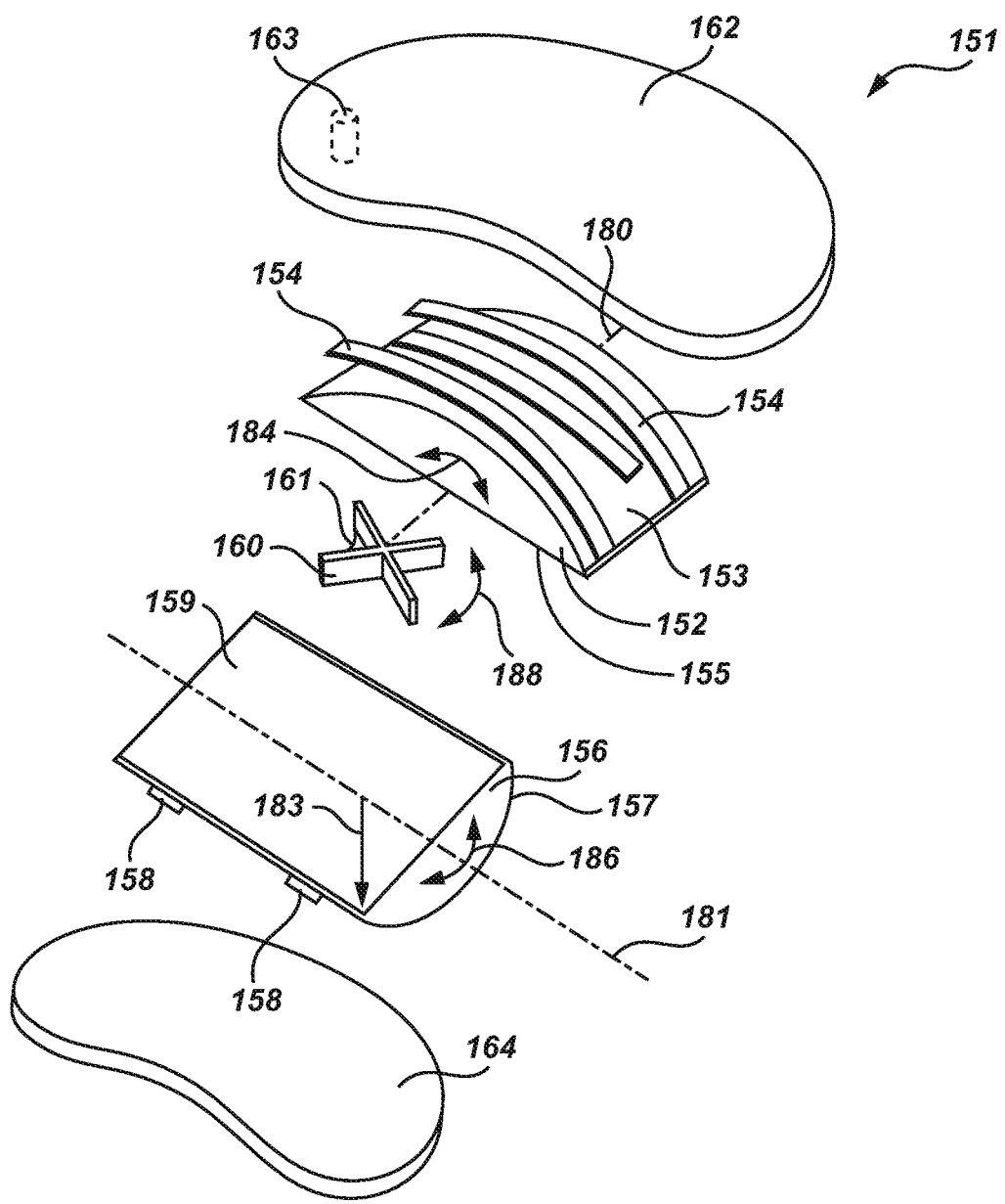
FIG. 10 is an exploded isometric view of the spinal implant of FIG. 9.
Figure 11:
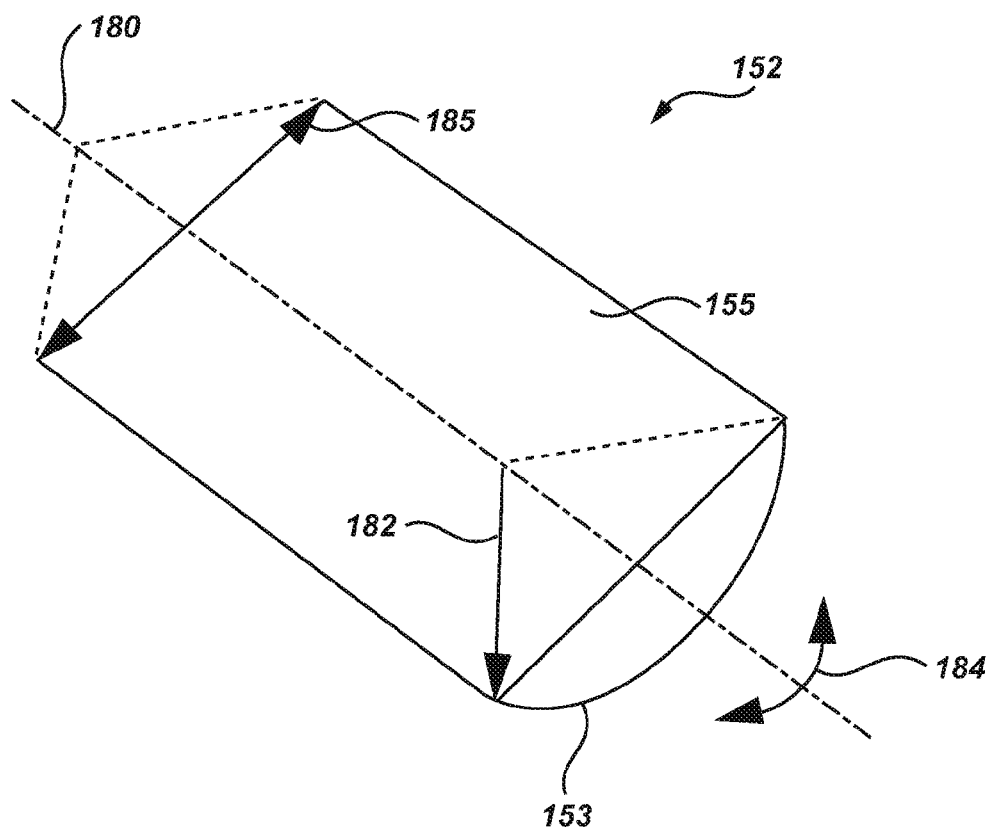
FIG. 11 is an isometric view of a rolling-contact core of the spinal implant of FIG. 9.

Further details of the embodiments of the spinal implant 150, 151 are illustrated in FIGS. 9-11. A first rolling-contact core 152 includes a first rolling surface 153 and a first chord surface 155, as best illustrated in FIG. 11. The embodiment of the first rolling surface 153 as illustrated is a portion of a cylindrical segment defined by a first radius of curvature 182 with a first axis 180, the first rolling surface 153 providing a first rolling motion in a direction 184. The first chord surface 155 is a plane through the cylindrical segment. The width 185 of the first rolling-contact core 152 can equal the diameter of the cylinder, or twice the first radius of curvature 182, in those embodiments in which the first chord surface 155 bisects the cylindrical segment through the first axis 180. While the first rolling surface 153 is illustrated to be defined by the first radius of curvature 182 and, therefore, circular in shape, it is understood that the first rolling surface 153 can be defined by a parabola, ellipsoid, toroid, hyperbolic, or other curved surface. The first rolling surface 153 can optionally be of a shape engineered and selected to provide a desired range of motion, instantaneous axis of rotation, helical axis of motion, kinematic response, resistance to motion, and the like.

Optionally, the spinal implant 150, 151 includes a second rolling-contact core 156, which includes a second rolling surface 157 and a second chord surface 159, as best illustrated in FIG. 10. The embodiment of the second rolling surface 157 as illustrated is a cylindrical segment defined by a second radius of curvature 183 with a second axis 181 that provides a second rolling motion in a direction 186. The second chord surface 159 is a plane through the cylindrical segment. While the second rolling surface 157 is illustrated to be defined by a second radius of curvature 183 and, therefore, circular in shape, it is understood that the second rolling surface 157 can be defined by a parabola, ellipsoid, toroid, hyperbolic, or other curved surface. The second rolling surface 157 can optionally be of a shape engineered and selected to provide a desired range of motion, instantaneous axis of rotation, helical axis of motion, kinematic response, resistance to motion, and the like. In addition, the second rolling surface 157 can be of a different geometry and have a different, second radius of curvature 183 (or other defining characteristic, such as the major and minor axis of an ellipsoid, or the focus of a parabola, as non-limiting examples) than the geometry and first radius of curvature 181 of the first rolling surface 155.

The second rolling-contact core 156, when included, is oriented such that the second axis 181 is rotated relative to the first axis 180 such that the second rolling motion occurs in a second, different direction 186 relative to the first rolling motion that occurs in the first direction 184. The first axis 180 and second axis 181 can be rotated relative to each other from about 0 degrees to about 180 degrees and, more preferably, from about 30 degrees to about 150 degrees and, more preferably still, from about 70 degrees to about 110 degrees, as well as orthogonal to each other. For example, a spinal implant 150, 151 can be provided that allows rolling motion in flexion-extension (e.g., around the X-axis 60 in FIG. 5), as well as lateral extension/bending (e.g., around the Y-axis 63 in FIG. 5).

The spinal implant 150, 151 can be formed of biocompatible plastics, polymers, metals, metal alloys, laminates, shape-memory materials, and other similar materials, either wholly as one material or as a combination of materials—i.e., different components may be manufactured from different materials and/or a single component, such as a rolling-contact core, can be manufactured of two or more materials, such as have a softer or resilient outer surface over a more rigid inner material. Optionally, the materials can be resilient. That is, the materials can have a varying and selectable degree of elastic deformation to provide cushioning between the vertebra 106 and 108 in order to mimic, at least in part, the cushioning that intervertebral discs 120 provide to the spinal segment 100.

Optionally, the first rolling-contact 152 core includes at least one flexure 154, and the second rolling-contact core 156 optionally includes at least another flexure 158. That is, one or more flexures 154, 158 can be used to create what may be referred to as a compliant mechanism or compliant spinal implant because its motion occurs, in part, through the flexible deflection of the flexures, as is described below. For example, FIGS. 9 and 10 illustrate the use of three flexures 154, 158 on the respective rolling-contact cores 152, 156. As illustrated, the flexures 154, 158 are disposed on the first rolling surface 153 and the second rolling surface 157, respectively, although they can be positioned elsewhere. The flexures 154, 158 optionally can be made from a different material or the same material as the rolling-contact cores. The flexures 154, 158 optionally can be formed as flexible bands of a resilient or elastic material. That is, the flexures 154, 158 optionally exhibit elastic, spring-like behavior. The flexures 154, 158 optionally can be formed of biocompatible plastics, polymers, metals, metal alloys, laminates, shape-memory materials, and other similar materials, either wholly as one material or as a combination of materials—i.e., different components may be manufactured from different materials.

The flexures 154, 158 optionally are formed by separating a strip of material from the respective rolling-contact core 152, 156. Alternatively, the flexures 154, 158 are coupled to the respective rolling surface 153, 157 by welding, adhesives, mechanical connectors, and the like at a first end of the flexure 154, 158. At another end of the flexure spaced apart from the first end, the flexure 154, 158 is coupled to either an end plate or directly to a vertebra through the use of bio-compatible adhesives, mechanical connectors, such as screws, welding, and the like.

The flexures 154, 158 provide, in part, a spring-like constraint to the rolling motion in the directions 184 and 186, respectively. That is, the further the rolling motion occurs, the greater the restoring force that the flexures 154, 158 impart to the rolling-contact core 152, 156 to return the rolling-contact core 152, 156 to a neutral or undeflected position. In addition, the flexures 154, 158, maintain, in part, the relative position of the rolling-contact core 152, 156 to either the vertebrae 106, 108 and/or the end plates 162, 164. That is, the flexures 154, 158 allow rolling motion, but limit, in part, the ability of the rolling-contact core 152, 156 to move laterally, posteriorly, or anteriorly out of position relative to the vertebrae 106, 108.

The flexures 154, 158 as noted optionally couple the rolling-contact cores 152, 156 directly to the vertebrae 106, 108, whether through adhesives or mechanical devices, such as screws. The flexures 154, 158 can be attached at the vertebral end plate, within the area of the vertebra bounded by the vertebral end plate, or elsewhere on the vertebra, including the pedicles and/or the spinous process, and the like. The rolling surfaces 153, 157 would then roll directly upon the vertebra 106, 108.

Alternatively, the flexures 154, 158 can be coupled to the device end plates 162, 164 by mechanical devices, such as screws and the like, adhesives, welding, slots into which the ends of the flexures are retained, such as by clamping, and such other methods and systems. The rolling surfaces 153, 157 then roll upon a surface of the end plates 162, 164. The end plates 162, 164 can be square, rectangular, shaped like the vertebra 106, 108, as illustrated in FIG. 10, or other such shapes.

The end plates 162, 164 can be formed of biocompatible plastics, polymers, metals, metal alloys, laminates, shape-memory materials, and other similar materials, either wholly as one material or as a combination of materials, such as having a softer or resilient outer surface over a more rigid inner material. Optionally, the materials can be flexible and/or resilient. That is, the materials can have a varying and selectable degree of elastic deformation to provide cushioning between the vertebra 106 and 108 in order to mimic, at least in part, the cushioning that intervertebral discs 120 provide to the spinal segment 100. Further, resilient end plates 162, 164 optionally distribute the compressive load borne by the spinal implant 150 across a larger percentage of the area within the vertebral end plates, which may reduce the degree or the risk of remodeling of the cancellous tissue of the vertebra. Alternatively, the end plates 162, 164 optionally distribute the compressive load to the vertebral end plates.

The end plates 162, 164 operably couple the flexures 154, 158 and the rolling-contact cores 152, 156, respectively, to the first vertebra 106 and the second vertebra 108. More preferably, the end plates 162, 164 are not just operably coupled the vertebra, but also secured to the vertebra which indicates a direct connection to the vertebra, whereas operably coupled can include either a direct or indirect connection to the vertebra. The end plates 162, 164 can be secured via adhesives and/or mechanical devices, such as bone screws that can be installed in the optional through-holes 163 (FIG. 10). Optionally, threaded anchors can be screwed into the vertebra (and/or spinous process, and/or pedicles, and other such locations of the vertebra and spine), the threaded anchor then being threaded into a blind hole (not illustrated). Other similar examples of mechanical systems fall within the scope of the disclosure.

Figure 14:
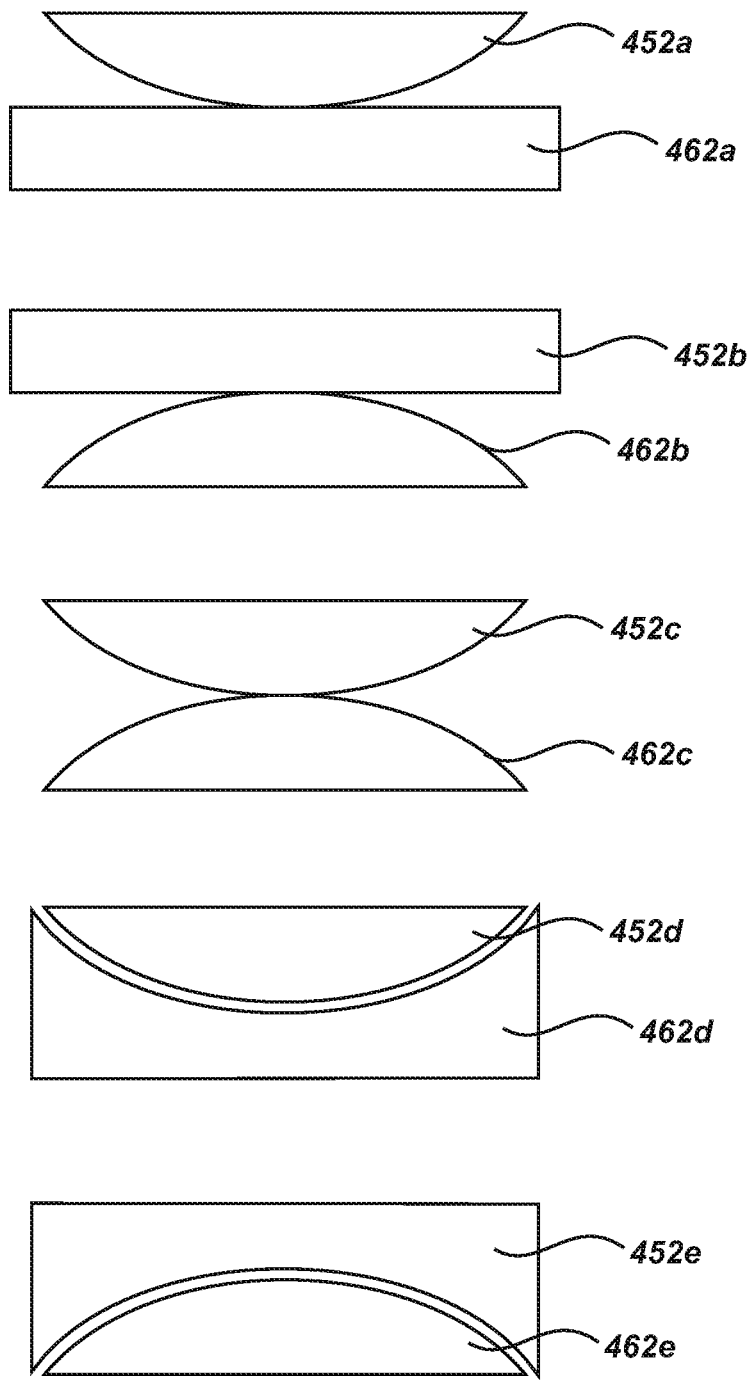

It is noted that the above embodiments describe rolling-contact cores 152, 156 that include a curved surface and end plates 162, 164 of substantially planar surfaces. Of course, other embodiments of rolling-contact cores and end plates fall within the scope of the disclosure. Non-limiting examples of such embodiments are illustrated in FIG. 14 and include: a rolling-contact core 452a that includes a convex surface and a substantially planar end plate 462a; a substantially planar rolling-contact core 452b and a convex end plate 462b; a convex rolling-contact core 452c and a convex end plate 462c; a convex rolling-contact core 452d and a concave end plate 462d; and a concave rolling-contact core 452e and a convex end plate 462e. Of course combinations, such as rolling-contact cores and end plates of different configurations and combinations fall within the scope of the disclosure. Further, these other embodiments of rolling-contact cores and end plates optionally use the flexures described above to constrain, at least in part, the motion of the rolling-contact cores. In addition, these other embodiments of rolling-contact cores and end plates optionally use an axial rotation core as described below.

Figure 1:
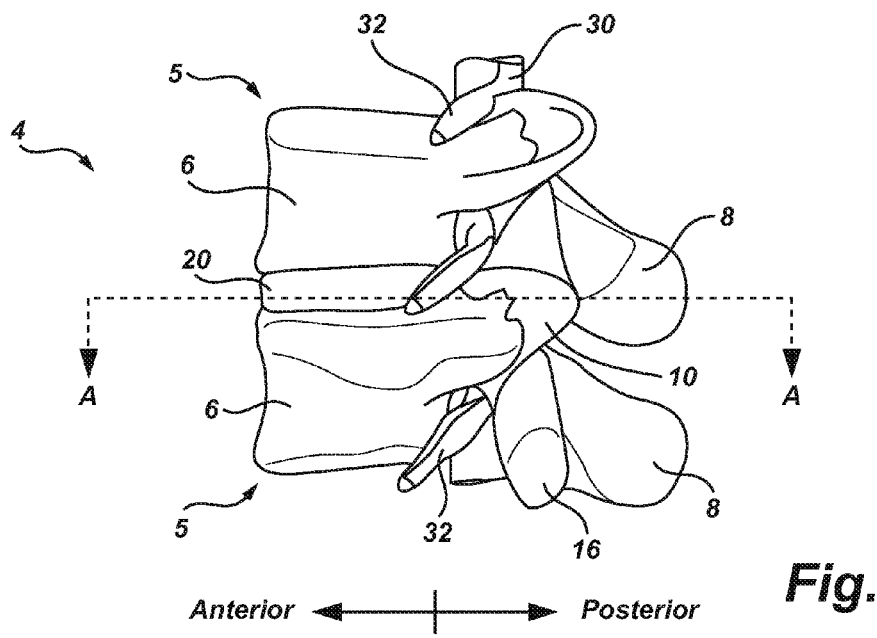
FIG. 1 is a segment of a functional spine unit.
Figure 2:
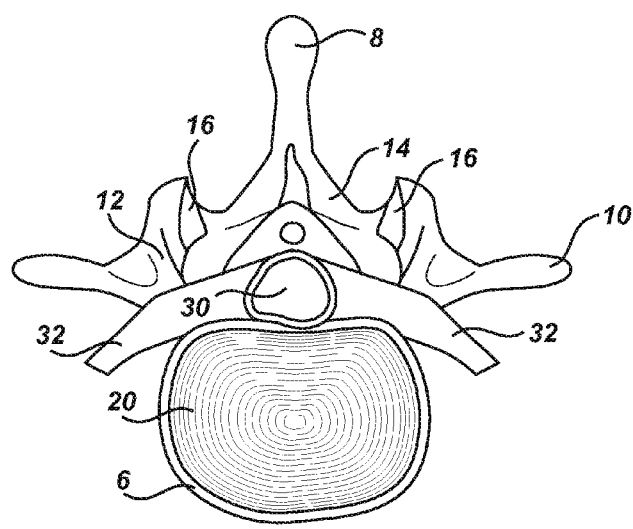
FIG. 2 is a cross-section of the segment of the functional spine unit illustrated in FIG. 1, taken along section A-A of FIG. 1.
Figure 3:
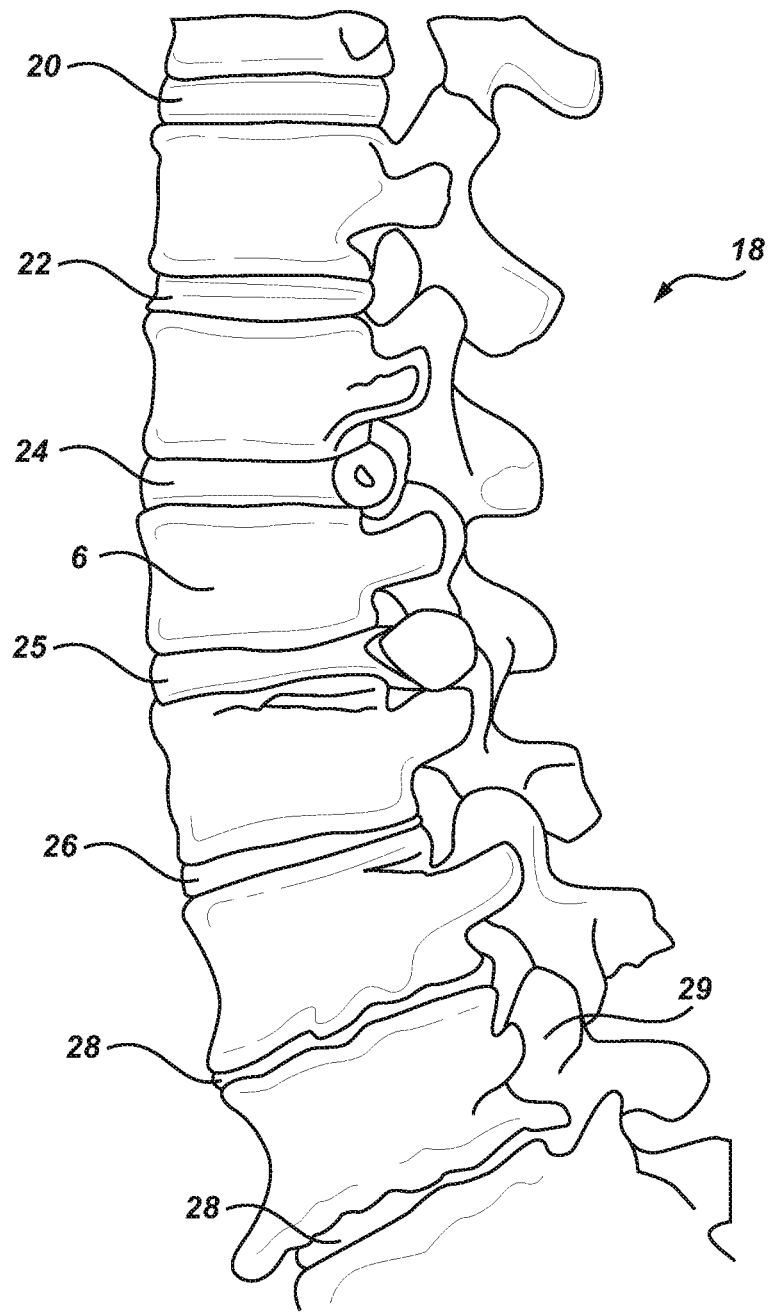
FIG. 3 is a segment of a spine illustrating various pathologies of intervertebral discs.
Figure 4:
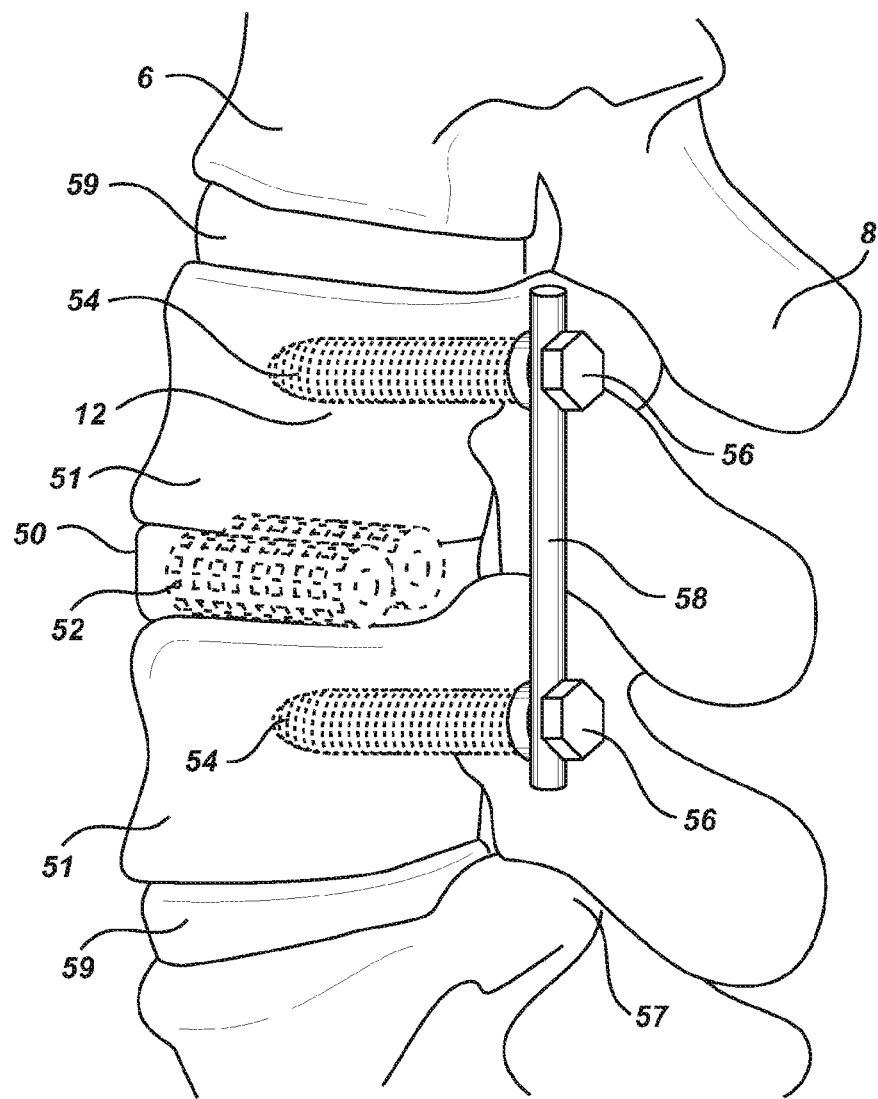
FIG. 4 is a prior art discectomy and spinal fusion.
Figure 5:
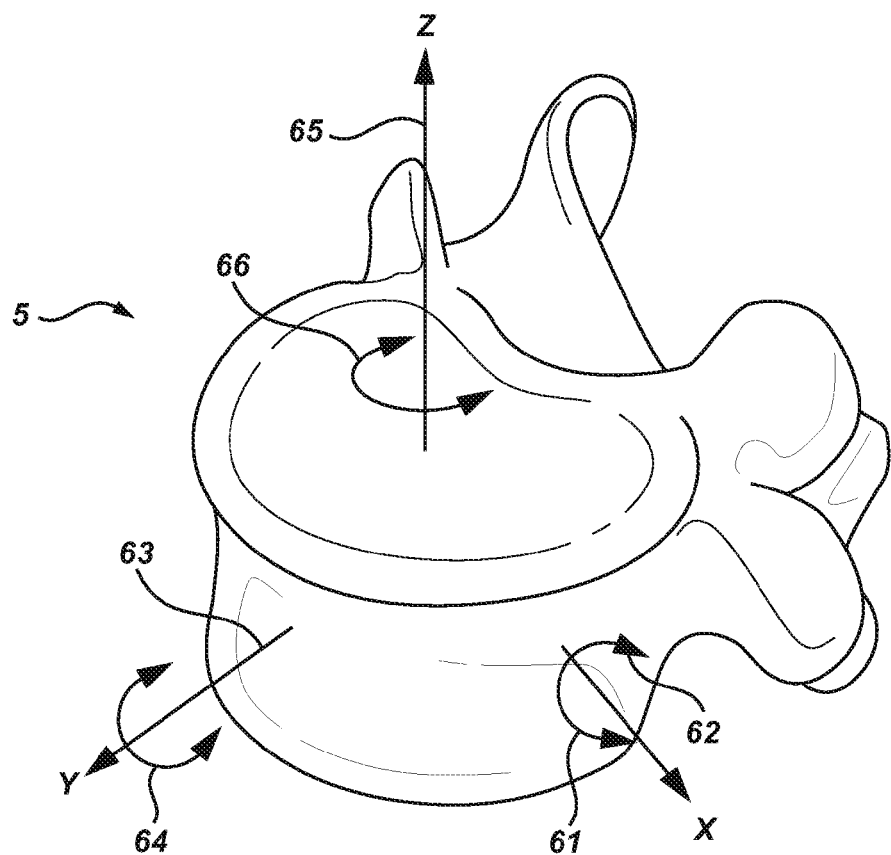
FIG. 5 illustrates the three axes of motion around which a functional spine unit moves.
Figure 6:
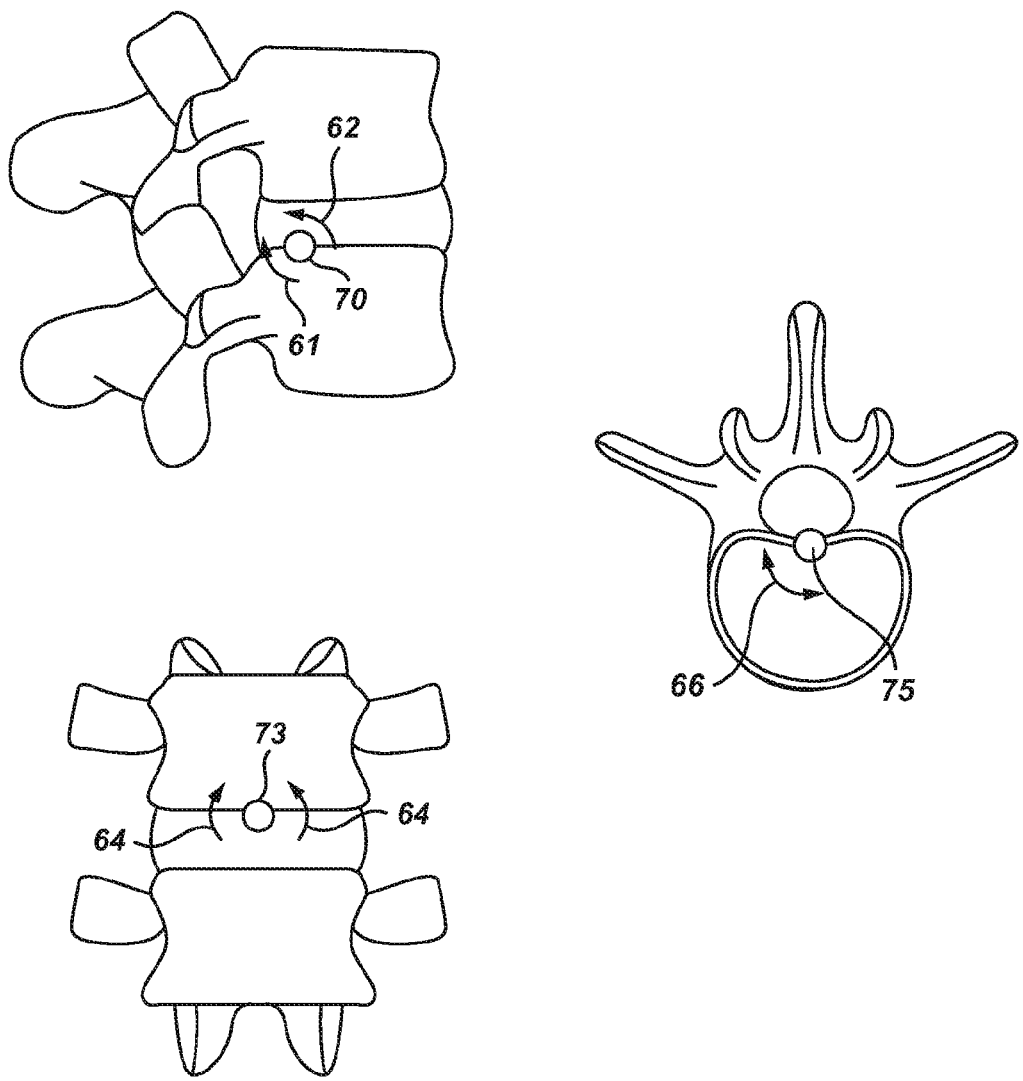
FIG. 6 illustrates the centers-of-motion of a functional spine unit.
Figure 12:
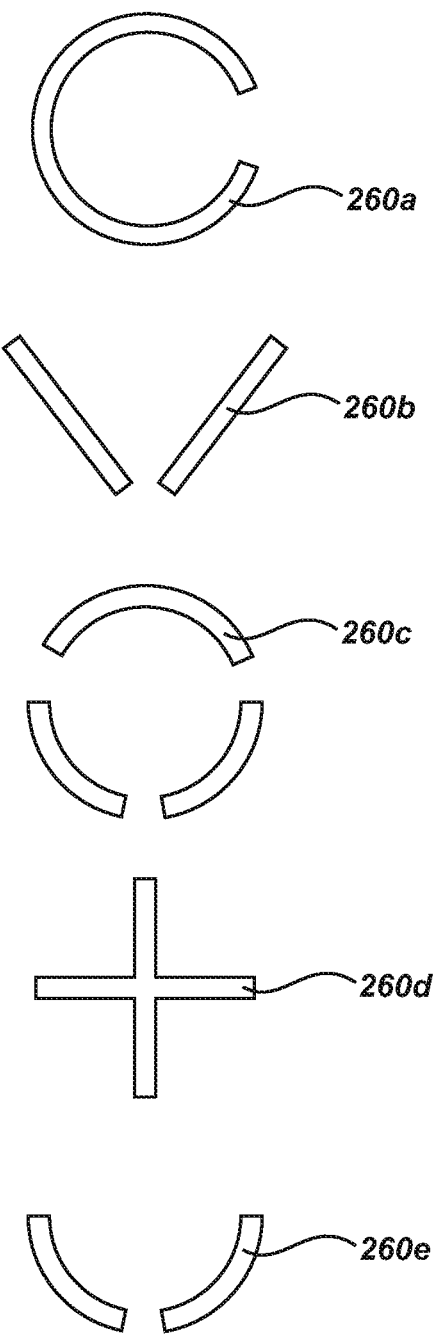
FIG. 12 is a top view of several embodiments of the axial-rotation core.

Optionally, the spinal implant 150, 151 includes an axial-rotation core 160 configured to provide axial rotation in a direction 188 (FIG. 10) of a first vertebra relative to a second vertebra, such as vertebra 106, 108, respectively. The axial rotation can, for example, occur around the Z-axis 65 as illustrated in FIG. 5, i.e., orthogonal to the first axis 180 and the second axis 181. The axial-rotation core 160 can optionally be of a shape engineered and selected to provide a desired range of motion, instantaneous axis of rotation, helical axis of motion, kinematic response, resistance to motion, and the like. For example, while FIGS. 9 and 10 illustrate an embodiment of an axial-rotation core 160 that is a cross or cruciform in shape, other non-limiting examples of embodiments include those illustrated in FIG. 12, such as 260a (a split-ring); 260b (a split-V); 260c (another split ring, in three portions); 260d (cross or cruciform); and 260e (one-half of split-ring). Other shapes fall within the scope of the disclosure.

The axial-rotation core 160 can be formed of biocompatible plastics, polymers, metals, metal alloys, laminates, shape-memory materials, and other similar materials, either wholly as one material or as a combination of materials. Optionally, the materials can be resilient. That is, the materials can have a varying and selectable degree of elastic deformation to provide cushioning between the vertebra 106 and 108 in order to mimic, at least in part, the cushioning that intervertebral discs 120 provide to the spinal segment 100. The axial-rotation core 160 can be formed to be an integral part of one or more of the rolling-contact cores 152, 156, or it can be a separate component coupled, either directly or indirectly, to the rolling-contact cores 152, 156, such as through the use of adhesives and mechanical connecting devices, such as screws, welding, and the like.

Embodiments of the axial-rotation core 160 include those that are positioned between a rolling-contact core and a vertebra (not illustrated) and/or an end plate 162, 164. Other embodiments include positioning the axial-rotation core 160 between two rolling-contact cores 152, 156 as illustrated in FIGS. 9 and 10. Other positions of the axial-rotation core 160 relative to the vertebra and the spinal implant 150, 151 and its components fall within the scope of the disclosure.

Optionally, the axial-rotation core 160 includes at least one axial or third flexure 161 and, optionally, more flexures 161. The axial flexure(s) 161 can be coupled, directly or indirectly, to various parts of the axial-rotation core 160, as illustrated in FIG. 10. Alternatively, the axial flexure 161 optionally can couple, in part, the axial-rotation core 160 to at least one of the rolling-contact cores, such as the first rolling-contact core 152 as illustrated in FIG. 9. In yet other embodiments, the axial flexure(s) 161 couple the axial-rotation core 160 to one or more of the end plates 162, 164 and/or the vertebra itself, such as the vertebra 106, 108, and/or its vertebral endplates, and/or the pedicles, and/or the spinous process, and the like. The coupling of the axial flexure(s) 161 optionally can be achieved through the use of mechanical devices, such as screws and the like, adhesives, welding, slots into which the flexures are retained, such as by clamping, and such other methods and systems.

The axial flexure(s) 161 optionally can be made from a different material or the same material as the axial-rotation cores 160. The axial flexure(s) 161 optionally can be formed as flexible bands of a resilient or elastic material. That is, the axial flexure(s) 161 optionally exhibit elastic, spring-like behavior. The axial flexure(s) 161 optionally can be formed of biocompatible plastics, polymers, metals, metal alloys, laminates, shape-memory materials, and other similar materials, either wholly as one material or as a combination of materials—i.e., different components may be manufactured from different materials.

The axial flexure(s) 161 provide, in part, a spring-like constraint to axial rotation in the direction 188. That is, the greater the axial rotation, the greater the restoring force that the axial flexure(s) 161 impart to the axial-rotation core 160 to return the axial-rotation core 160 to a neutral or undeflected position. In addition, the axial flexure(s) 161 maintain, in part, the relative position of the axial-rotation core 160 to either the vertebrae 106, 108 and/or the end plates 162, 164. That is, the axial flexure(s) 161 allow axial rotation, but limit, in part, the ability of the axial-rotation core 160 to move laterally, posteriorly, or anteriorly out of position relative to the vertebrae 106, 108.

Figure 13:
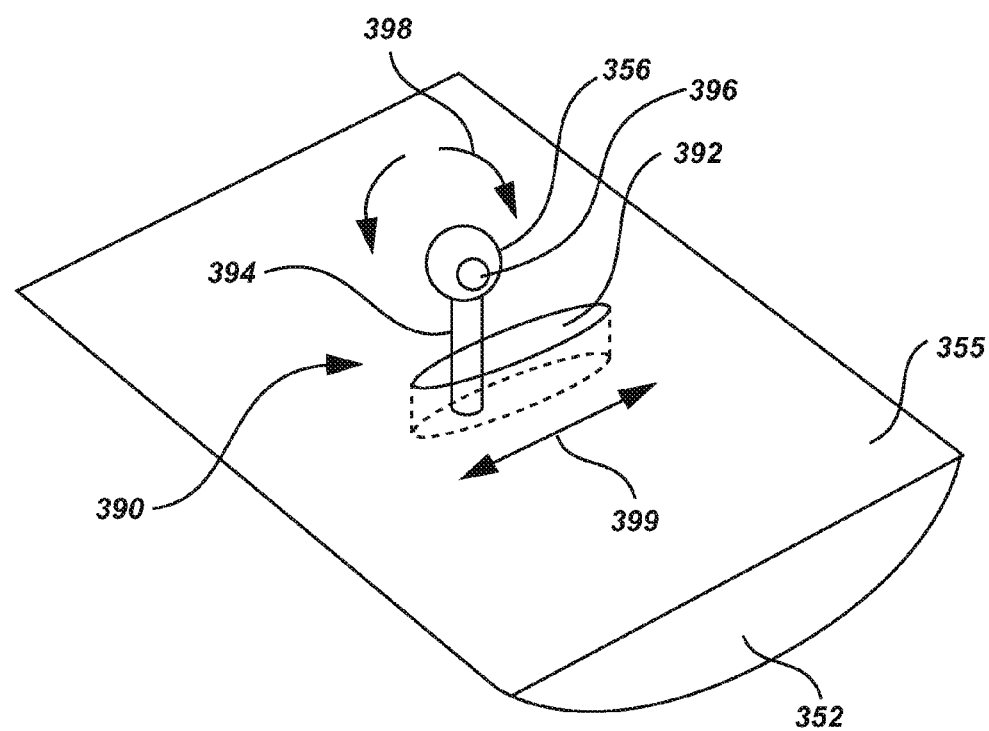
FIG. 13 is an isometric view of another embodiment, a pin-in-slot joint, of the axial-rotation core and an embodiment of a rolling-contact core; and, FIG. 14 is a side view of several embodiments of rolling-contact cores and end plates.

Another embodiment of the axial-rotation core is illustrated in FIG. 13. The axial-rotation core 390 is a pin-in-slot joint. That is, the axial-rotation core 390 includes a slot 392 formed within the chord surface 355 of a rolling-contact core 352. The slot 392 is oriented to provide lateral movement in a direction 399 that, for example, may correspond to the Y-axis 63 in FIG. 5. A pin 394 is configured to be received and retained at a first end within the slot 392. The pin 392 is coupled at the connection 396 to, for example, a rolling-contact core 356, of which only a small portion is illustrated for clarity. The pin 394 is configured to rotate in a direction 398 around, for example, the Z-axis 65 in FIG. 5, thereby imparting a relative axial rotation between the rolling-contact cores 352, 356 and, consequently, the vertebrae coupled thereto. Thus, the axial-rotation core 390 provides a center-of-rotation that is capable of translation in a lateral direction while also providing axial rotation.

Optionally, the axial-rotation core 390 includes axial flexures (not illustrated in FIG. 13), such as those axial flexure(s) 161 discussed above.

Embodiments of the spinal implant disclosed herein provide additional benefits, such as:

Kinetics similar to a healthy spine: Embodiments of the spinal implant provide relative motion to vertebra in the three axes discussed above regarding FIG. 5 similar to that of a healthy spine. One result of this benefit is that the patient's muscles and ligaments do not have to compensate for an unnatural motion of the spinal implant, unlike the case with prior art devices. In other words, the spinal implant provides more natural motion, which would encourage patients to move more with less attendant pain as their muscles would not be compensating or overworking for a prior art spinal implant that does not provide such natural motion around all three axes.

Kinematics similar to a healthy spine: Related to the kinetics are the natural kinematics of embodiments of the spinal implants. As discussed above, the centers-of-rotation for flexion-extension, lateral extension/bending, and axial rotation, are each located in different places. Prior art devices cannot accommodate these separate centers-of-rotation around more than one axis, if even that; nor can they provide for the instantaneous or near instantaneous change in the location of the centers-of-motion as a spinal segment moves; nor can they provide for motion approximate the motion of a natural helical axis. Stated differently, the center-of-rotation of prior art devices is often in a different location than the natural center-of-rotation of the spine for a given movement. To compensate, patients with prior art devices suffered strain upon the spinal cord and peripheral nerves, muscle strain caused by the muscles overworking and compensating for the two different centers-of-rotation (that of the prior art device and that of the spine), ligament strain, and, consequently, pain. In contrast, embodiments of the present spinal implant provide centers-of-rotation in each of the three axes that are the same, or nearly the same, as a patient's natural centers-of-rotation for the spine. Thus, patients typically have less pain and, consequently, greater movement, to the benefit of the discs and the spine in general.

Adjust to the individual spine: As noted, embodiments of the spinal implant can be designed and/or selected preoperatively for an individual patient in order to provide implants that restore the diseased spine to near healthy function. That is, the particular geometry of the spinal implant and its components can be individually tailored to a particular patient and the particular location within the patient's spine at which the spinal implant is to be implanted.

Thus, disclosed above, in addition to the embodiments of the spinal implant are methods of treating a spine with a spinal implant, such as an intervertebral disc prosthesis, configured to provide motion in three axes and that provides kinetics and kinematics similar to that of a functional spine, as well as other methods that will be recognized by one of skill in the art.

As alluded to above, embodiments of methods of using the spinal implant are disclosed. While the spinal implants disclosed herein can be positioned within a spinal segment by using an anterior, posterior, or lateral approach in the patient, a preferred method is to use a posterior approach. Further, it is preferred that a minimally invasive procedure be used, such as by laparoscopy in which only one or a few, small incisions are made and the surgery is conducted with laparoscopic tools. The methods include making an incision; providing an embodiment of the spinal implant disclosed herein; positioning the spinal implant between a first vertebra and a second vertebra; and coupling the spinal implant to at least the first vertebra. Securing the spinal implant to the vertebrae may be done by applying straps, applying biocompatible adhesives, installing pedicle screws, and the like, as known in the art.

The present invention, in various embodiments, includes providing devices and processes in the absence of items not depicted and/or described herein or in various embodiments hereof, including in the absence of such items as may have been used in previous devices or processes, e.g., for improving performance, achieving ease and/or reducing cost of implementation.

The foregoing discussion of the invention has been presented for purposes of illustration and description. The foregoing is not intended to limit the invention to the form or forms disclosed herein. In the foregoing Detailed Description for example, various features of the invention are grouped together in one or more embodiments for the purpose of streamlining the disclosure. This method of disclosure is not to be interpreted as reflecting an intention that the claimed invention requires more features than are expressly recited in each claim. Rather, as the following claims reflect, inventive aspects lie in less than all features of a single foregoing disclosed embodiment. Thus, the following claims are hereby incorporated into this Detailed Description, with each claim standing on its own as a separate preferred embodiment of the invention.

Moreover, though the description of the invention has included description of one or more embodiments and certain variations and modifications, other variations and modifications are within the scope of the invention, e.g., as may be within the skill and knowledge of those in the art, after understanding the present disclosure. It is intended to obtain rights which include alternative embodiments to the extent permitted, including alternate, interchangeable and/or equivalent structures, functions, ranges or steps to those claimed, whether or not such alternate, interchangeable and/or equivalent structures, functions, ranges or steps are disclosed herein, and without intending to publicly dedicate any patentable subject matter.

What is claimed is:

1. A spinal implant comprising:
   a first rolling-contact core operable to be coupled to a first vertebra, the first rolling contact core having a first convex surface having a first axis and a chord surface intersecting the first convex surface, the first convex surface configured to provide a first rolling motion in a first direction to the first vertebra relative to a second vertebra;
a plurality of flexible elongate flexures configured to constrain the first rolling motion, each elongate flexure comprising:
a first end directly fixedly attached to the first rolling-contact core; and
a second end spaced apart from the first end and fixedly attached to or adapted to be fixedly attached to an element selected from the group consisting of:
the first vertebra; and
an end plate adapted to be affixed to the first vertebra;
wherein fixed attachment of each of the plurality of elongate flexures to the first rolling-contact core and the first vertebra or the end plate is adapted to constrain relative movement at a point of contact between the first rolling-contact core and the first vertebra or the end plate to non-translational rolling movement.

2. A spinal implant as recited in claim 1, wherein a first of the plurality of elongate flexures is fixedly attached proximate a first side of the first rolling-contact core, and a second of the plurality of elongate flexures is fixedly attached proximate a second side of the first rolling-contact core opposite the first side.

3. A spinal implant as recited in claim 1, wherein the plurality of elongate flexures comprise three elongate flexures.

4. A spinal implant as recited in claim 1, wherein the first convex surface of the first rolling contact core is adapted to provide the point of contact between the first rolling-contact core and the first vertebra or the end plate.

5. A spinal implant as recited in claim 4, wherein as the first rolling contact core rolls across the first vertebra or the end plate, the point of contact between the first convex surface of the first rolling contact core and a corresponding surface of the first vertebra or end plate translates across the corresponding surface without substantial translation of the convex surface relative to the corresponding surface at the point of contact.

6. A spinal implant as recited in claim 1, wherein the second end of each flexure is adapted to be fixedly attached to the first vertebra.

7. A spinal implant as recited in claim 1, further comprising the end plate, and wherein the second end of each flexure is fixedly attached to or adapted to be fixedly attached to the end plate.

8. A spinal implant as recited in claim 1, wherein a fixed attachment between each flexure and the first rolling contact core and a fixed attachment between each flexure and the vertebra or end plate is selected from the group consisting of:
a fixed attachment formed by separating a strip of material from the rolling contact core except at a point of fixed attachment to form the flexure;
a fixed attachment formed by welding;
a fixed attachment formed by an adhesive;
a fixed attachment formed by a mechanical connector;
a fixed attachment formed by a slot into which an end of the flexure is inserted and retained; and
a clamp.

9. A spinal implant as recited in claim 1, further comprising:
a second rolling-contact core operable to be coupled to the second vertebra, the second rolling-contact core having a second convex surface having a second axis rotated relative to the first axis, the second convex surface configured to provide a second rolling motion in a second direction to the first vertebra relative to the second vertebra;
an elongate flexure configured to constrain the second rolling motion, the elongate flexure being flexible and comprising:
a first end fixedly attached to the second rolling-contact core; and
a second end spaced apart from the first end and fixedly attached to or adapted to be fixedly attached to an element selected from the group consisting of:
the second vertebra; and
an end plate adapted to be affixed to the second vertebra;
wherein fixed attachment of the elongate flexure to the second rolling-contact core and the second vertebra or the second vertebra end plate is adapted to constrain relative movement at a point of contact between the second rolling-contact core and the second vertebra or the second vertebra end plate to non-translational rolling movement.

10. A spinal implant as recited in claim 9, further comprising:
the two end plates adapted to be fixedly secured to the first and second vertebrae and attached to or adapted to be fixedly attached to the elongate flexures of the first and second rolling-contact cores, respectively.

11. A spinal implant as recited in claim 9, wherein the second rolling-contact core is operably coupled to the first rolling-contact core.

12. A spinal implant as recited in claim 11, wherein the second rolling-contact core is coupled to the first rolling-contact core through an axial-rotation core.

13. A spinal implant comprising:
a first rolling-contact core operable to be coupled to a first vertebra, the first rolling-contact core having a first convex surface having a first axis and a chord surface intersecting the first convex surface, the first convex surface configured to provide a first rolling motion in a first direction to the first vertebra relative to a second vertebra;
a plurality of flexible elongate flexures configured to constrain the first rolling motion, each elongate flexure comprising:
a first end directly fixedly attached to the first rolling-contact core; and
a second end spaced apart from the first end and fixedly attached to or adapted to be fixedly attached to an element selected from the group consisting of:
the first vertebra; and
an end plate adapted to be affixed to the first vertebra;
wherein at least one of the elongate flexures is fixedly attached proximate a first edge of the first convex surface, and wherein a different at least one of the elongate flexures is fixedly attached proximate a second edge of the first convex surface that is opposite the first edge of the first convex surface.

14. A spinal implant as recited in claim 13, wherein fixed attachment of the elongate flexures to the first rolling-contact core and the first vertebra or the end plate is adapted to constrain relative movement at a point of contact between the first rolling-contact core and the first vertebra or the end plate to non-translational rolling movement.

15. A spinal implant as recited in claim 13, wherein the first convex surface of the first rolling contact core is adapted to provide the point of contact between the first rolling-contact core on the one hand and the first vertebra or the end plate on the other hand.

16. A spinal implant as recited in claim 15, wherein as the first rolling contact core rolls across the first vertebra or the end plate, the point of contact between the first convex surface of the first rolling contact core and a corresponding surface of the first vertebra or end plate translates across the corresponding surface without substantial translation of the convex surface relative to the corresponding surface at the point of contact.

17. A spinal implant as recited in claim 13, wherein the second end of each flexure is adapted to be fixedly attached to the first vertebra.

18. A spinal implant as recited in claim 13, further comprising the end plate, and wherein the second end of each flexure is fixedly attached to or adapted to be fixedly attached to the end plate.

19. A spinal implant as recited in claim 13, wherein a fixed attachment between each flexure and the first rolling contact core and a fixed attachment between each flexure and the vertebra or end plate is selected from the group consisting of:
  a fixed attachment formed by separating a strip of material from the rolling contact core except at a point of fixed attachment to form the flexure;
  a fixed attachment formed by welding;
  a fixed attachment formed by an adhesive;
  a fixed attachment formed by a mechanical connector;
  a fixed attachment formed by a slot into which an end of the flexure is inserted and retained; and
  a clamp.

20. A spinal implant as recited in claim 13, further comprising:
  a second rolling-contact core operable to be coupled to the second vertebra, the second rolling-contact core having a second convex surface having a second axis rotated relative to the first axis, the second convex surface configured to provide a second rolling motion in a second direction to the first vertebra relative to the second vertebra;
  a plurality of elongate flexures configured to constrain the second rolling motion, each elongate flexure comprising:
    a first end fixedly attached to the second rolling-contact core; and
    a second end spaced apart from the first end and fixedly attached to or adapted to be fixedly attached to an element selected from the group consisting of:
      the second vertebra; and
      an end plate adapted to be affixed to the second vertebra;
  wherein at least one of the elongate flexures is fixedly attached proximate a first edge of the first convex surface, and wherein a different at least one of the elongate flexures is fixedly attached proximate a second edge of the first convex surface that is opposite the first edge of the first convex surface.

21. A spinal implant as recited in claim 20, further comprising:
  the two end plates adapted to be fixedly secured to the first and second vertebrae and attached to or adapted to be fixedly attached to the elongate flexures of the first and second rolling-contact cores, respectively.

22. A spinal implant as recited in claim 20, wherein the second rolling-contact core is operably coupled to the first rolling-contact core.

23. A spinal implant as recited in claim 22, wherein the second rolling-contact core is coupled to the first rolling-contact core through an axial-rotation core.

24. A spinal implant comprising:
  a first rolling-contact core operable to be coupled to a first vertebra, the first rolling-contact core having a first surface and a chord surface intersecting the first surface, the first surface configured to provide a first rolling motion in a first direction to the first vertebra relative to a second vertebra;
  a plurality of flexible elongate flexures configured to constrain the first rolling motion, each elongate flexure comprising:
    a first end directly fixedly attached to the first rolling-contact core; and
    a second end spaced apart from the first end and fixedly attached to or adapted to be fixedly attached to an element selected from the group consisting of:
      the first vertebra; and
      an end plate adapted to be affixed to the first vertebra;
  wherein fixed attachment of each of the plurality of elongate flexures to the first rolling-contact core and the first vertebra or the end plate is adapted to constrain relative movement at a point of contact between the first rolling-contact core and the first vertebra or the end plate to non-translational rolling movement.

25. A spinal implant as recited in claim 24, wherein a first of the plurality of elongate flexures is fixedly attached proximate a first side of the first rolling-contact core, and a second of the plurality of elongate flexures is fixedly attached proximate a second side of the first rolling-contact core opposite the first side.

26. A spinal implant as recited in claim 24, wherein the plurality of elongate flexures comprise three elongate flexures.

27. A spinal implant as recited in claim 24, wherein the first surface of the first rolling contact core is adapted to provide the point of contact between the first rolling-contact core on the one hand and the first vertebra or the end plate on the other hand.

28. A spinal implant as recited in claim 27, wherein as the first rolling contact core rolls across the first vertebra or the end plate, the point of contact between the first surface of the first rolling contact core and a corresponding surface of the first vertebra or end plate translates across the corresponding surface without substantial translation of the convex surface relative to the corresponding surface at the point of contact.

29. A spinal implant as recited in claim 24, wherein the first surface of the first rolling contact core is convex.

30. A spinal implant as recited in claim 24, further comprising:
  a second rolling-contact core operable to be coupled to the second vertebra, the second rolling-contact core having a second surface, the second surface configured to provide a second rolling motion in a second direction to the first vertebra relative to the second vertebra;
  an elongate flexure configured to constrain the second rolling motion, the elongate flexure comprising:
    a first end fixedly attached to the second rolling-contact core; and
    a second end spaced apart from the first end and fixedly attached to or adapted to be fixedly attached to an element selected from the group consisting of:
      the second vertebra; and
      an end plate adapted to be affixed to the second vertebra;

wherein fixed attachment of the elongate flexure to the second rolling-contact core and the second vertebra or the second vertebra end plate is adapted to constrain relative movement at a point of contact between the second rolling-contact core and the second vertebra or the second vertebra end plate to non-translational rolling movement.

31. A spinal implant as recited in claim 30, wherein the second rolling-contact core is operably coupled to the first rolling-contact core.

* * * * *